(12) United States Patent
Haas

(10) Patent No.: US 9,078,708 B2
(45) Date of Patent: Jul. 14, 2015

(54) IMPLANT FOR MUTUALLY SUPPORTING THE SPINOUS PROCESSES OF ADJACENT VERTEBRAL BODIES AND A SURGICAL SYSTEM

(75) Inventor: Alexander Haas, Donaueschingen (DE)

(73) Assignee: Aesculap AG, Tuttlingen (DE)

( * ) Notice: Subject to any disclaimer, the term of this patent is extended or adjusted under 35 U.S.C. 154(b) by 310 days.

(21) Appl. No.: 13/558,789

(22) Filed: Jul. 26, 2012

(65) Prior Publication Data

US 2013/0023933 A1 Jan. 24, 2013

Related U.S. Application Data

(63) Continuation of application No. PCT/EP2010/070360, filed on Dec. 21, 2010.

(30) Foreign Application Priority Data

Jan. 27, 2010 (DE) .......................... 10 2010 000 231

(51) Int. Cl.
*A61B 17/70* (2006.01)

(52) U.S. Cl.
CPC .................................. *A61B 17/7065* (2013.01)

(58) Field of Classification Search
USPC ............................. 606/248, 249, 90, 99, 86 A
See application file for complete search history.

(56) References Cited

U.S. PATENT DOCUMENTS

| 3,648,691 | A | 3/1972 | Lumb et al. |
| 5,351,792 | A | 10/1994 | Cohen |
| 5,645,589 | A | 7/1997 | Li |
| 6,214,050 | B1 | 4/2001 | Huene |
| 6,322,883 | B1 | 11/2001 | Williams |
| 6,332,883 | B1 | 12/2001 | Zucherman |
| 7,048,736 | B2 | 5/2006 | Robinson |
| 7,585,313 | B2 | 9/2009 | Kwak |

(Continued)

FOREIGN PATENT DOCUMENTS

| DE | 4411974 | 10/1995 |
| DE | 69431348 | 5/2003 |

(Continued)

OTHER PUBLICATIONS

PCT International Search Report for Application No. PCT/EP2010/070360 Dated Aug. 7, 2012.

(Continued)

*Primary Examiner* — Jerry Cumberledge
(74) *Attorney, Agent, or Firm* — RatnerPrestia

(57) ABSTRACT

An implant for supporting the spinous processes of adjacent vertebral bodies includes a first implant component and a second implant component and is transferable by moving the second implant component relative to the first implant component along a spreading direction from an introduction position into a spread position. The implant includes a locking device incorporating a locking element wherein the locking element is transferable relative to at least one implant component along a locking direction from a release position, in which the second implant component is movable relative to the first implant component in a direction opposed to the spreading direction, into a locking position in which the second implant component is locked to the first implant component. The implant also includes a securing device for securing the locking element against a movement that is directed counter to the locking direction.

25 Claims, 10 Drawing Sheets

(56) References Cited

U.S. PATENT DOCUMENTS

Figure 1:
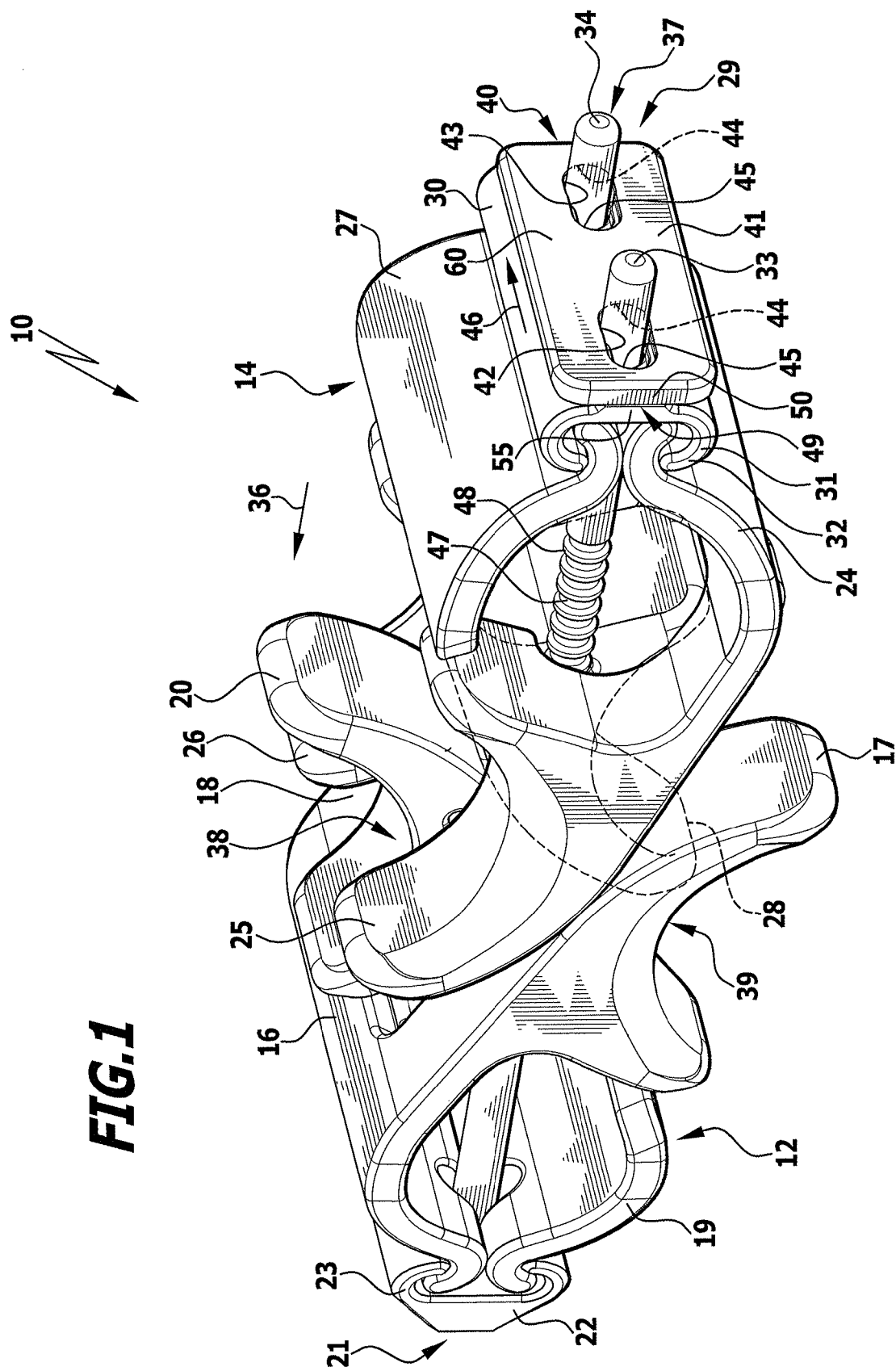

| | | | |
|---|---|---|---|
| 7,585,316 B2 | 9/2009 | Trieu | |
| 7,588,592 B2 | 9/2009 | Winslow | |
| 7,727,233 B2 | 6/2010 | Blackwell | |
| 7,811,307 B2 | 10/2010 | Deneuvillers | |
| 8,012,207 B2 | 9/2011 | Kim | |
| 8,128,659 B2 | 3/2012 | Ginsberg | |
| 8,262,697 B2 | 9/2012 | Kirschman | |
| 8,313,512 B2* | 11/2012 | Kwak et al. | 606/249 |
| 8,361,116 B2* | 1/2013 | Edmond | 606/249 |
| 2003/0040746 A1 | 2/2003 | Mitchell | |
| 2005/0033434 A1 | 2/2005 | Berry | |
| 2005/0055031 A1 | 3/2005 | Lim | |
| 2006/0084985 A1* | 4/2006 | Kim | 606/61 |
| 2006/0122611 A1 | 6/2006 | Morales | |
| 2006/0247640 A1 | 11/2006 | Blackwell | |
| 2007/0032790 A1* | 2/2007 | Aschmann et al. | 606/61 |
| 2007/0225724 A1 | 9/2007 | Edmond | |
| 2007/0225807 A1* | 9/2007 | Phan et al. | 623/17.11 |
| 2007/0233074 A1* | 10/2007 | Anderson et al. | 606/61 |
| 2007/0270840 A1 | 11/2007 | Chin | |
| 2007/0270856 A1 | 11/2007 | Morales | |
| 2008/0027438 A1 | 1/2008 | Abdou | |
| 2008/0086212 A1 | 4/2008 | Zucherman | |
| 2008/0108990 A1 | 5/2008 | Mitchell et al. | |
| 2008/0109082 A1 | 5/2008 | Fink | |
| 2008/0109802 A1 | 5/2008 | Carrigan | |
| 2008/0114367 A1 | 5/2008 | Meyer | |
| 2008/0183211 A1 | 7/2008 | Lamborne | |
| 2008/0183218 A1 | 7/2008 | Mueller | |
| 2008/0228225 A1 | 9/2008 | Trautwein | |
| 2008/0249569 A1 | 10/2008 | Waugh | |
| 2008/0281359 A1 | 11/2008 | Abdou | |
| 2008/0281360 A1 | 11/2008 | Vittur | |
| 2008/0300601 A1 | 12/2008 | Fabian | |
| 2008/0306488 A1 | 12/2008 | Altarac et al. | |
| 2009/0018658 A1 | 1/2009 | Garcia | |
| 2009/0138055 A1 | 5/2009 | Altarac et al. | |
| 2009/0149886 A1 | 6/2009 | Zentes et al. | |
| 2009/0265006 A1 | 10/2009 | Seifert | |
| 2009/0292316 A1* | 11/2009 | Hess | 606/249 |
| 2009/0326581 A1* | 12/2009 | Galley et al. | 606/249 |
| 2010/0004688 A1 | 1/2010 | Maas et al. | 606/248 |
| 2010/0131009 A1* | 5/2010 | Roebling et al. | 606/249 |
| 2010/0198245 A1 | 8/2010 | Haas et al. | |
| 2011/0009904 A1* | 1/2011 | Froehlich et al. | 606/249 |
| 2011/0160772 A1 | 6/2011 | Arcenio | |
| 2011/0160773 A1* | 6/2011 | Aschmann et al. | 606/249 |
| 2012/0089184 A1 | 4/2012 | Yeh | |
| 2012/0150228 A1 | 6/2012 | Zappacosta | |
| 2012/0215261 A1 | 8/2012 | Massoudi | |
| 2012/0277796 A1* | 11/2012 | Gabelberger et al. | 606/249 |
| 2012/0290008 A1 | 11/2012 | Kirschman | |
| 2013/0066374 A1* | 3/2013 | Galley et al. | 606/249 |
| 2013/0184753 A1 | 7/2013 | Keiper | |

FOREIGN PATENT DOCUMENTS

| | | |
|---|---|---|
| DE | 10326690 | 1/2005 |
| DE | 69828711 | 1/2006 |
| DE | 102004047566 B3 | 5/2006 |
| DE | 102004063996 | 8/2006 |
| DE | 202006018978 | 3/2007 |
| DE | 10 2007 052 799 A1 | 11/2007 |
| DE | 102006021025 | 1/2008 |
| DE | 20 2008 009 344 | 9/2008 |
| DE | 20 2009 001 321 | 2/2009 |
| EP | 0683653 | 9/2002 |
| EP | 1297792 | 4/2003 |
| EP | 2323574 | 2/2012 |
| GB | 2 436 292 | 9/2007 |
| WO | 2006102428 | 9/2006 |
| WO | WO 2006/111174 A1 | 10/2006 |
| WO | 2007070819 | 6/2007 |
| WO | WO 2007/127689 A2 | 11/2007 |
| WO | 2009127041 | 10/2009 |
| WO | 2010016949 | 2/2010 |
| WO | 2010019783 | 2/2010 |
| WO | 2010114925 | 10/2010 |
| WO | 2011031924 | 3/2011 |
| WO | 2012035275 | 3/2012 |

OTHER PUBLICATIONS

International Search Report for PCT/EP2011/069895 mailed Feb. 15, 2012.
International Search Report for Application No. PCT/EP2009/004844 dated Jan. 27, 2011.
International Search report of International Application No. PCT/EP2009/004844, Search Completed Oct. 28, 2009 (w/English language form PCT/ISA/210 to show relevance).
Search Report from the German Patent Office for Priority Patent Appklication No. DE 10 2008 032 685.2; Date of Conclusion of the Search, Jun. 8, 2009 (w/English translation of Form PCT/ISA/210.
Office Action for U.S. Appl. No. 13/372,033, dated Nov. 8, 2011.
Office Action for U.S. Appl. No. 13/891,378, mailed May 20, 2014.
Search Report for German Application No. 10 2010 000 231.3 Dated Sep. 21, 2010.
PCT International Search Report for Application No. PCT/EP2010/070360 Dated Dec. 21, 2010.
Notice of Allowance for U.S. Appl. No. 13/558,724, dated Dec. 11, 2014.
Office Action for U.S. Appl. No. 13/558,724, dated Oct. 7, 2014.
Office Action for U.S. Appl. No. 13/891,378, dated Sep. 25, 2014.

* cited by examiner

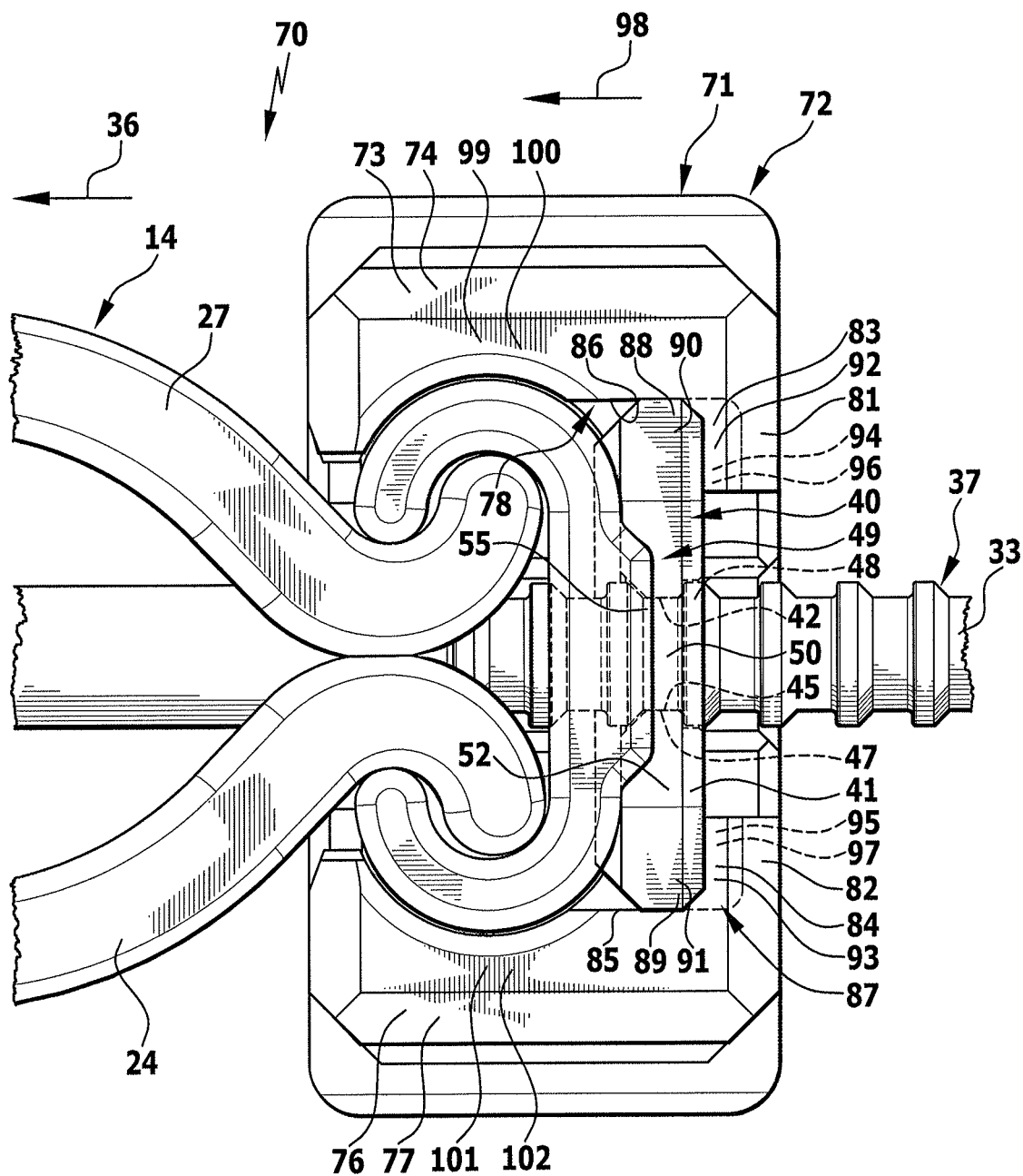

US 9,078,708 B2

IMPLANT FOR MUTUALLY SUPPORTING THE SPINOUS PROCESSES OF ADJACENT VERTEBRAL BODIES AND A SURGICAL SYSTEM

CROSS-REFERENCE TO RELATED APPLICATIONS

This application is a continuation under 35 U.S.C. §365 of international application number PCT/EP2010/070360, filed on Dec. 21, 2010, which claims priority to German application number 10 2010 000 231.3, filed Jan. 27, 2010. The contents of both applications are incorporated by reference herein in their entirety and for all purposes.

FIELD OF THE INVENTION

The present invention relates to an implant for mutually supporting the spinous processes of adjacent vertebral bodies. Moreover, the present invention relates to a surgical system comprising at least one implant of this type.

BACKGROUND OF THE INVENTION

An implant of the type mentioned hereinabove is described in DE 20 2008 009 344 U1, the entire content of which is hereby incorporated herein. It can be introduced into the gap between the spinous processes in an introduction position, and be transferred thereafter into a spread position. Thereby, the mutual spacing of the supporting surfaces increases so that the spinous processes resting on supporting surfaces can be pushed apart to a greater or lesser extent for stabilizing the adjacent vertebral bodies relative to each other. A locking device incorporating a locking element which is transferred from a release position into the locking position in the spread position of the implant serves for locking the implant, i.e. for locking the two implant components relative to each other. Hereby, the locking element can co-operate with at least one further locking element which is arranged on the first implant component in order to prevent a movement of the second implant component in a direction opposed to the spreading direction so that the second implant component is locked to the first implant component. In order to prevent the locking element from moving out of the locking position counter to the locking direction, the implant has a securing device. In the case of the implant described in DE 20 2008 009 344 U1, this is an additional component in the form of a cap which partly engages over the locking element and the second implant component. This must be attached manually by an operating surgeon after the processes of spreading and locking the implant for securing the locking element in the locking position.

An object underlying the present invention is, therefore, to further develop an implant and a surgical system in such a way as to provide a simpler means for securing the locking element from movement in a direction opposed to the locking direction.

SUMMARY OF THE INVENTION

In a first aspect of the invention, there is provided an implant for mutually supporting the spinous processes of adjacent vertebral bodies, comprising a first implant component and a second implant component. The implant is transferable by moving the second implant component relative to the first implant component along a spreading direction from an introduction position, in which the implant is introducible between an upper spinous process of an upper vertebral body and a lower spinous process of a lower vertebral body, into a spread position, in which an upper supporting surface for the upper spinous process that is formed by the implant and a lower supporting surface for the lower spinous process that is formed by the implant have a greater spacing relative to each other than in the introduction position. The implant comprises a locking device incorporating a locking element wherein the locking element is transferable relative to at least one implant component along a locking direction from a release position, in which the second implant component is movable relative to the first implant component in a direction opposed to the spreading direction, into a locking position in which the second implant component is locked to the first implant component against a movement that is directed counter to the spreading direction. The implant also comprises a securing device for securing the locking element against a movement that is directed counter to the locking direction. The securing device comprises at least one first securing member and also at least one second securing member which, following adoption of the locking position by the locking element, are transferable relative to one another in a securing direction that is directed transversely relative to the locking direction from an unsecured position, in which the at least one first securing member and the at least one second securing member do not co-operate, into a secured position in which the at least one first securing member and the at least one second securing member co-operate for securing the locking element. The locking element comprises the at least one first securing member and an implant component comprises the at least one second securing member.

In a second aspect of the invention, the invention relates to a surgical system comprising at least one implant of this type. The surgical system further comprises a handling device for transferring the locking element from the release position into the locking position.

BRIEF DESCRIPTION OF THE DRAWING FIGURES

Figure 2:
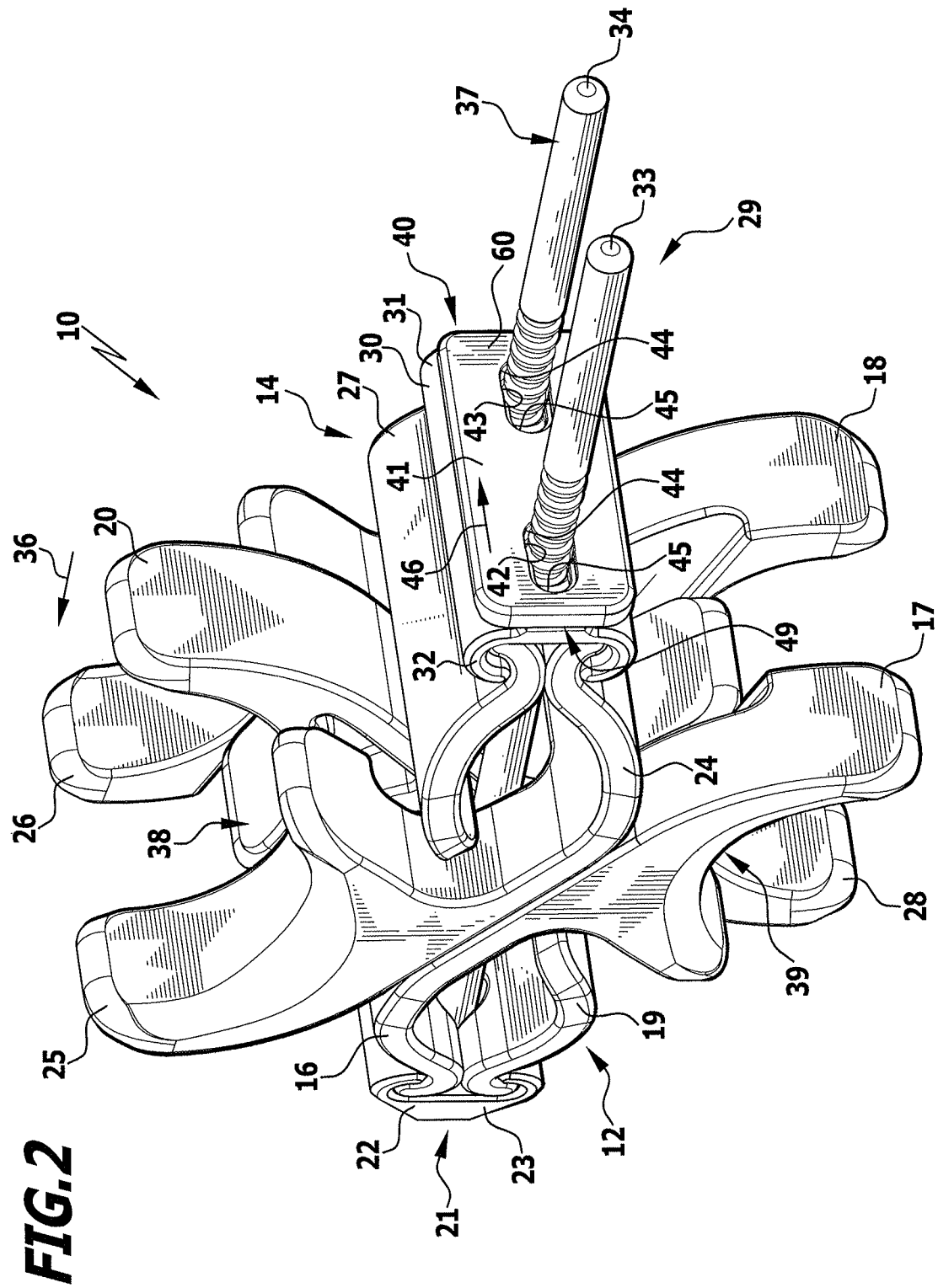
Figure 3:
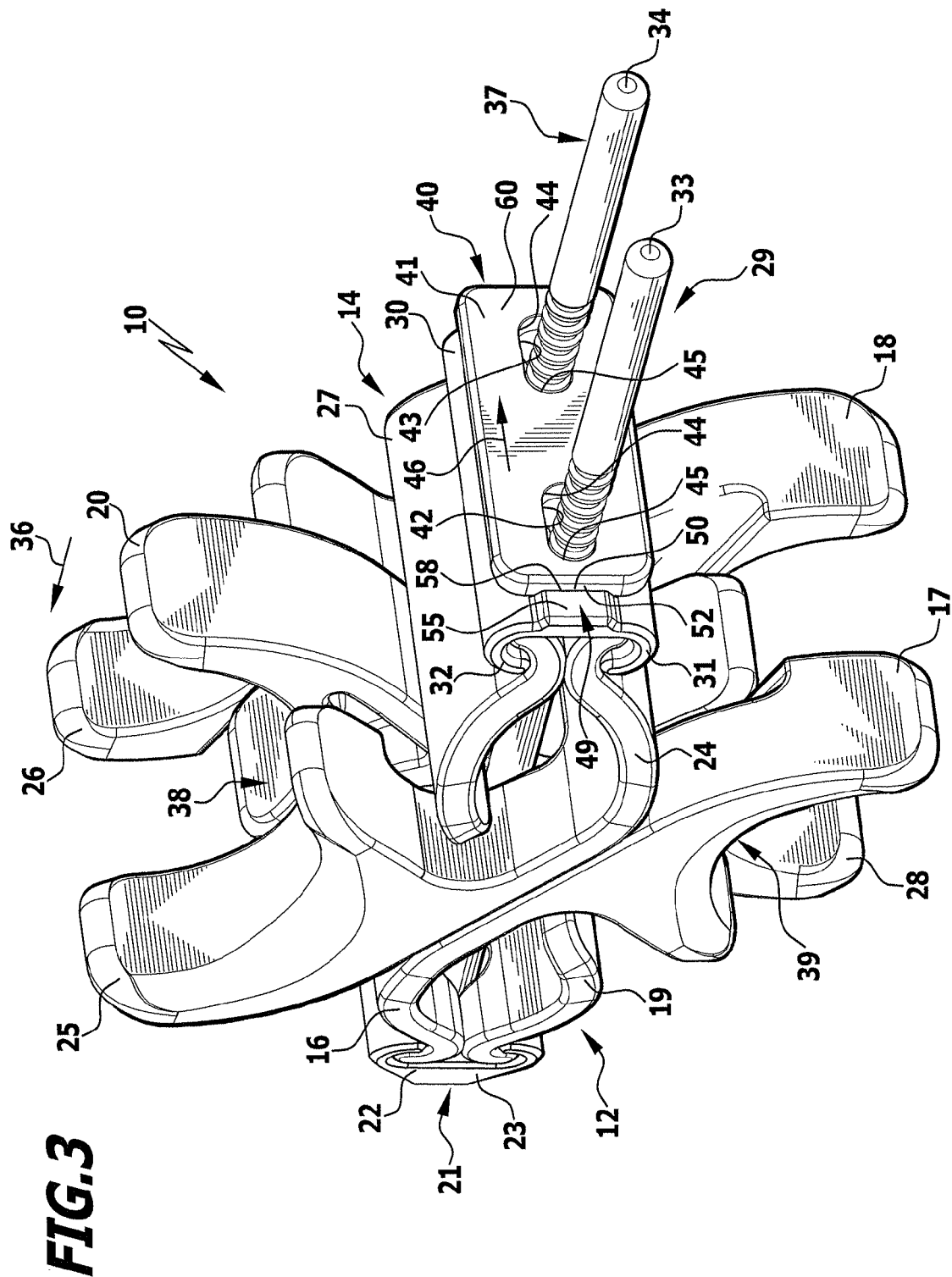
Figure 4:
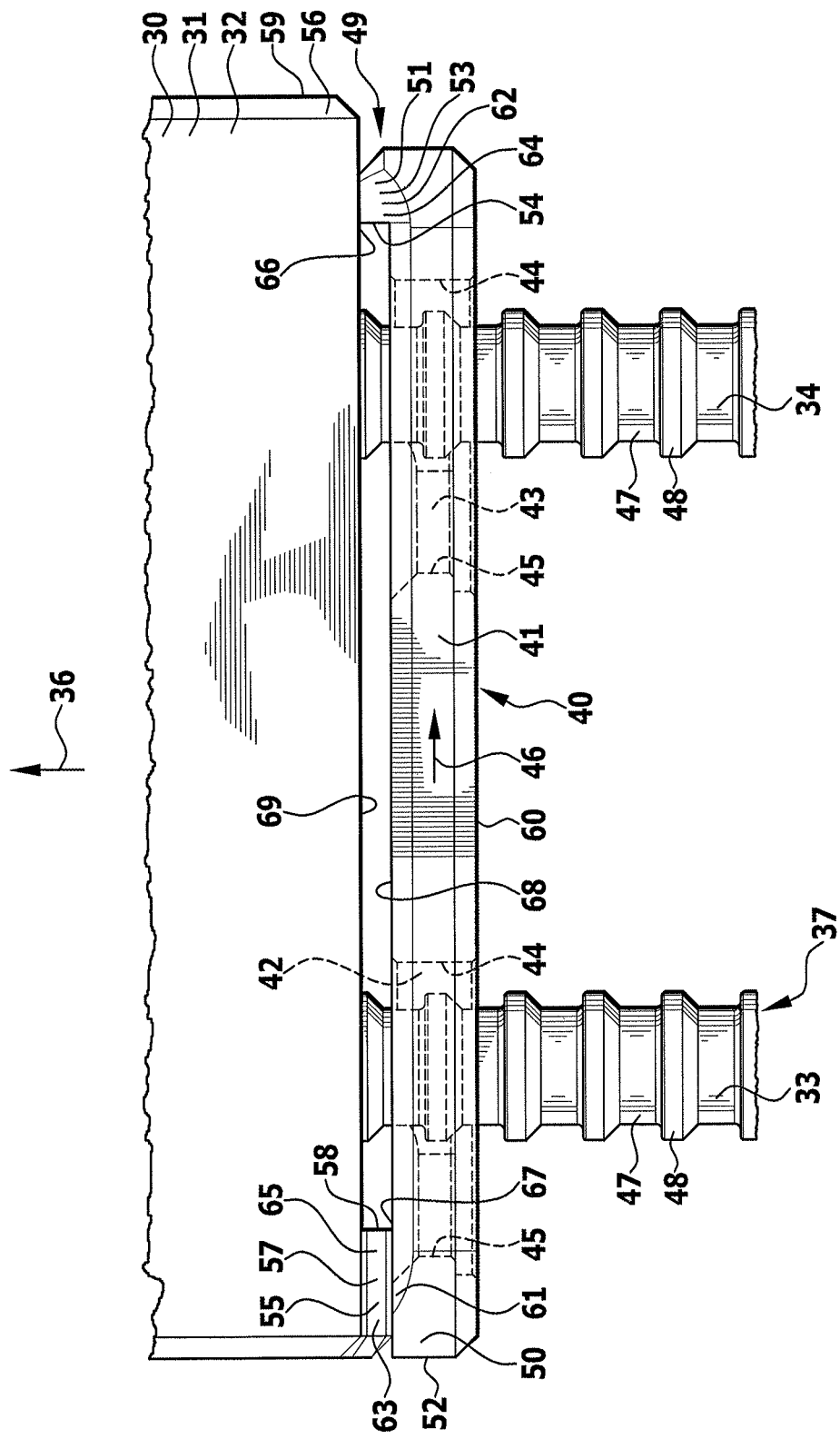
Figure 5:
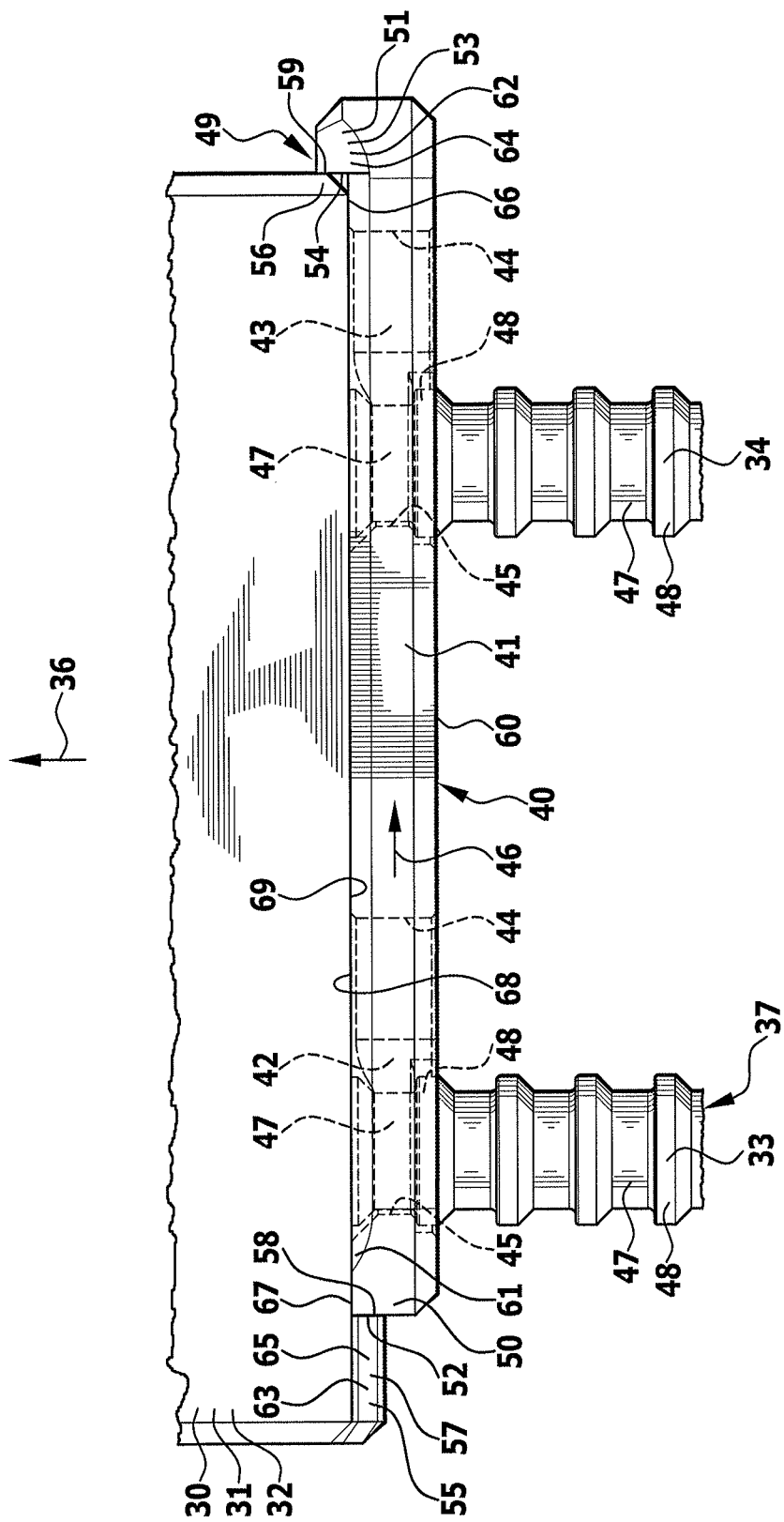
Figure 6:
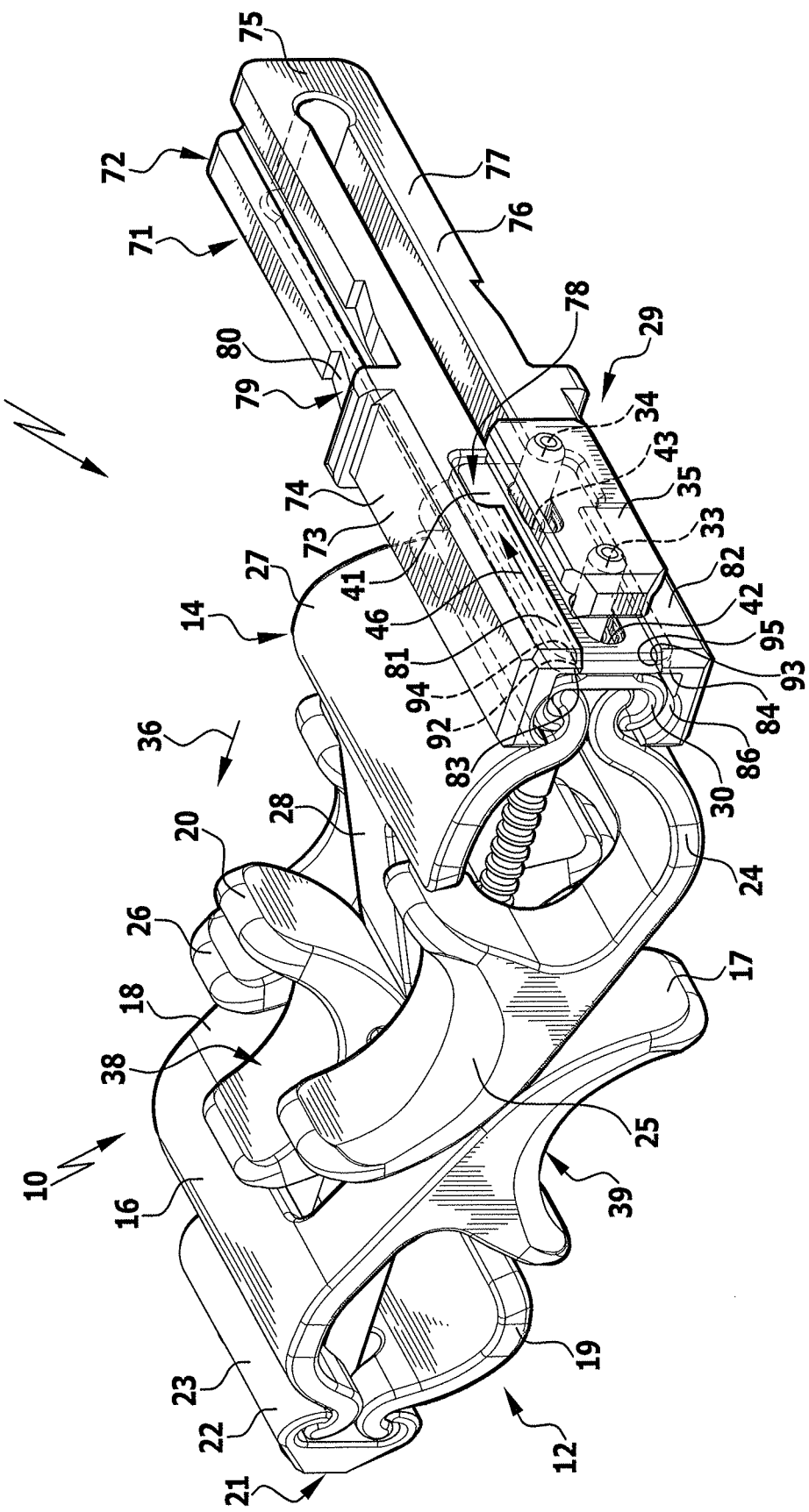
Figure 7:
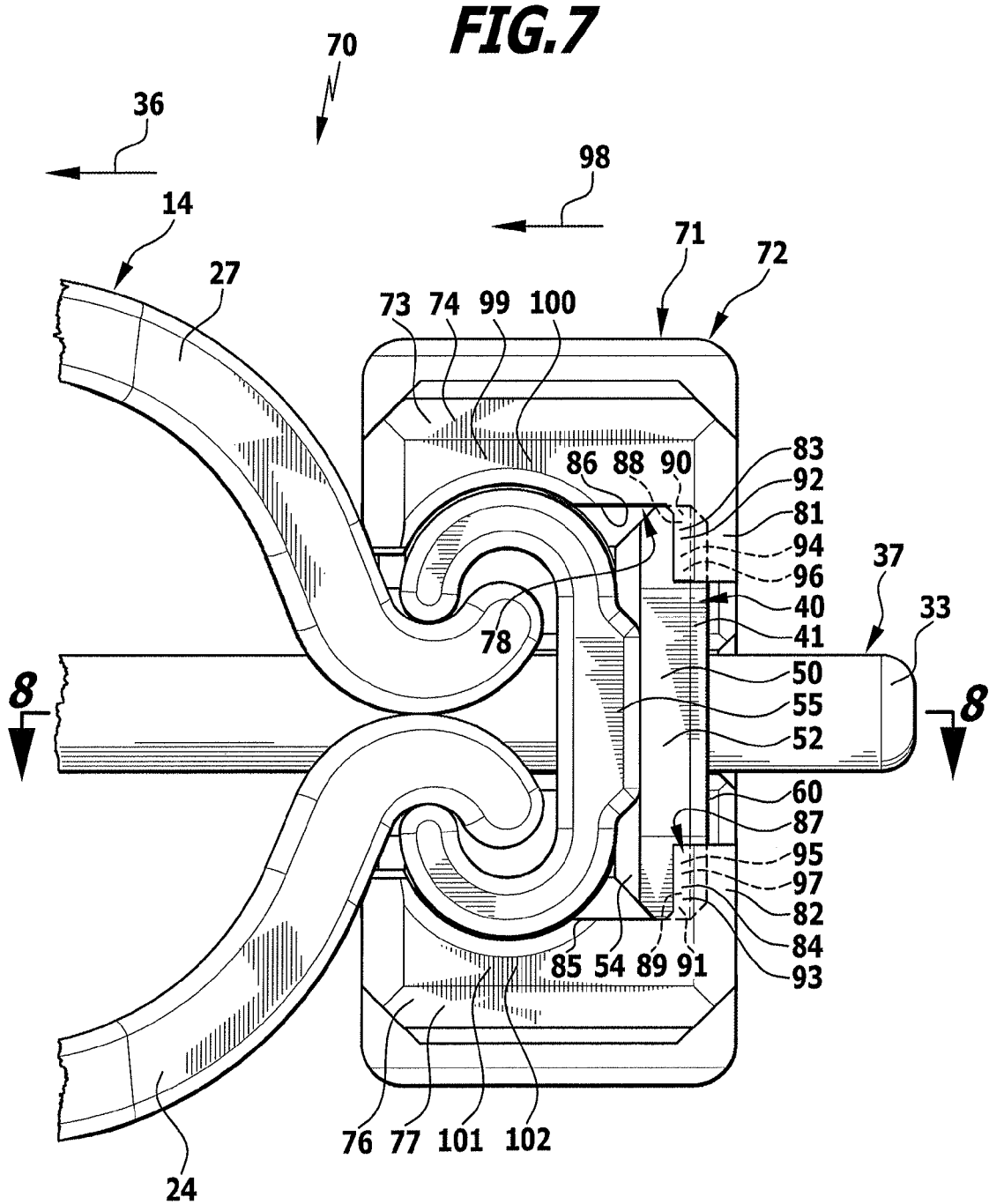
Figure 8:
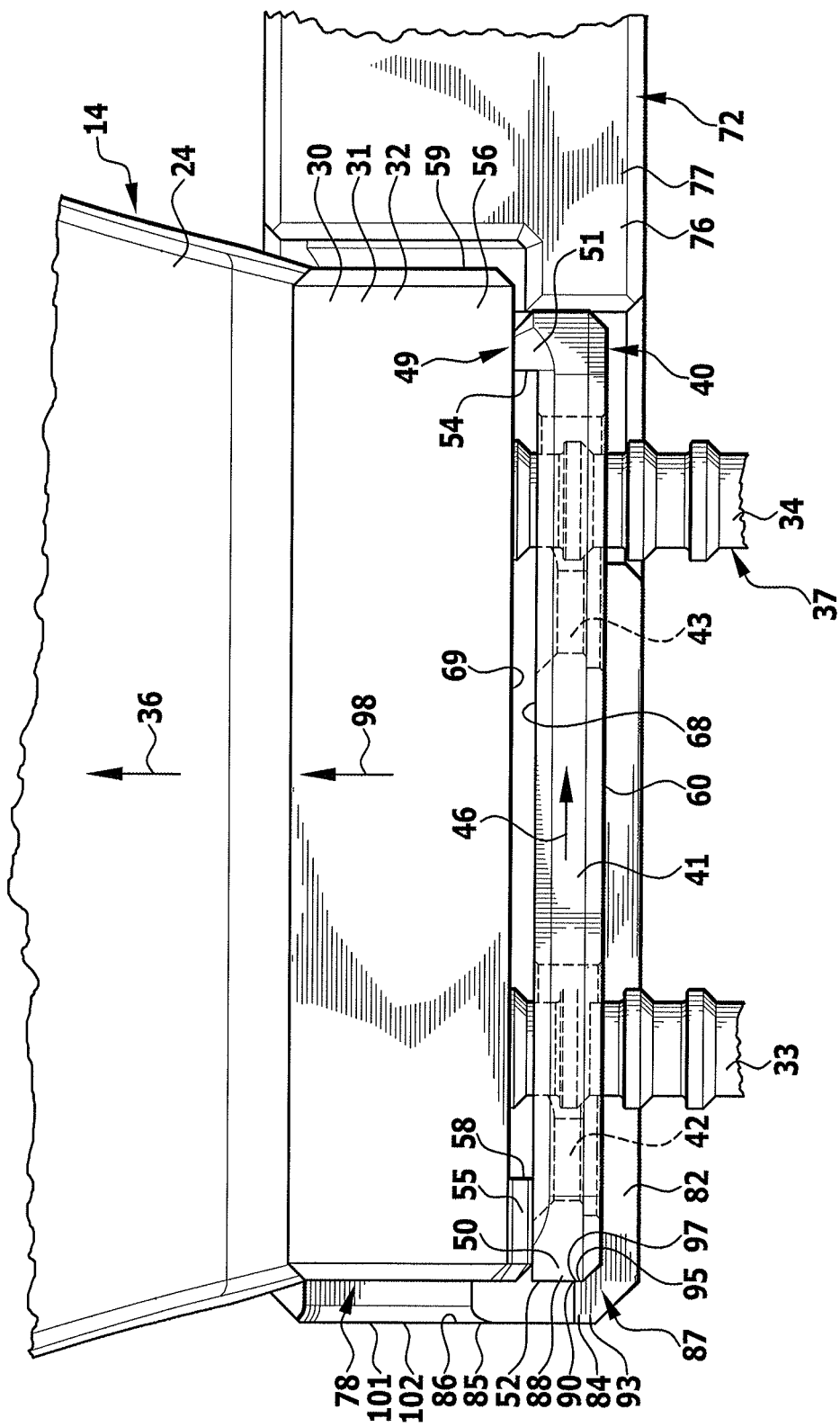
Figure 9:
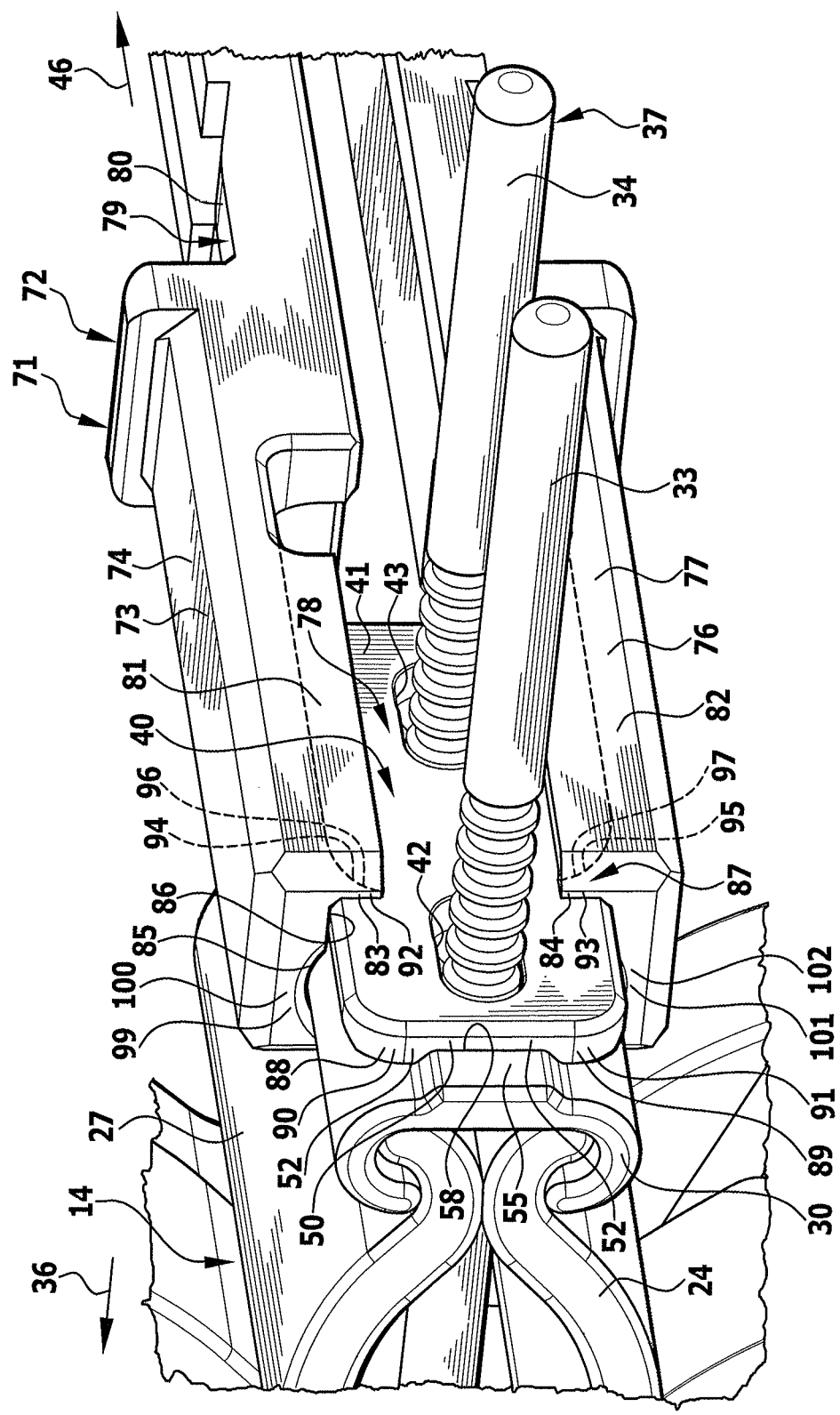

The foregoing summary and the following description may be better understood in conjunction with the drawing figures, of which:

FIG. 1: shows a perspective illustration of an implant in accordance with the an exemplary embodiment of the invention in an introduction position;

FIG. 2: a perspective illustration of the implant depicted in FIG. 1 in a spread position, wherein a locking element of the implant adopts a release position;

FIG. 3: the implant depicted in FIG. 2, wherein the locking element adopts a locking position;

FIG. 4: an enlarged plan view of a fixing element, the locking element and a tie rod of the implant depicted in FIG. 2;

FIG. 5: an enlarged plan view of the fixing element, the locking element and the tie rod of the implant depicted in FIG. 3;

FIG. 6: a perspective illustration of a surgical system in accordance with an exemplary embodiment of the invention, comprising the implant depicted in FIG. 1 and a handling device attached thereto;

FIG. 7: a partial side view of an end-side region of the surgical system depicted in FIG. 6;

FIG. 8: a sectional view along the line 8-8 in FIG. 7;

FIG. 9: a perspective partial illustration of the surgical system depicted in FIG. 6 when extracting the handling device from the implant; and FIG. 10: a side view of the surgical system similar to FIG. 7 when extracting the handling device from the implant.

DETAILED DESCRIPTION OF PREFERRED EMBODIMENTS OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to an implant for mutually supporting the spinous processes of adjacent vertebral bodies, comprising a first implant component and a second implant component. The implant is transferable by moving the second implant component relative to the first implant component along a spreading direction from an introduction position, in which the implant is introducible between an upper spinous process of an upper vertebral body and a lower spinous process of a lower vertebral body, into a spread position, in which an upper supporting surface for the upper spinous process that is formed by the implant and a lower supporting surface for the lower spinous process that is formed by the implant have a greater spacing relative to each other than in the introduction position. The implant comprises a locking device incorporating a locking element wherein the locking element is transferable relative to at least one implant component along a locking direction from a release position, in which the second implant component is movable relative to the first implant component in a direction opposed to the spreading direction, into a locking position in which the second implant component is locked to the first implant component against a movement that is directed counter to the spreading direction. The implant also comprises a securing device for securing the locking element against a movement that is directed counter to the locking direction. The securing device comprises at least one first securing member and also at least one second securing member which, following adoption of the locking position by the locking element, are transferable relative to one another in a securing direction that is directed transversely relative to the locking direction from an unsecured position, in which the at least one first securing member and the at least one second securing member do not co-operate, into a secured position in which the at least one first securing member and the at least one second securing member co-operate for securing the locking element. The locking element comprises the at least one first securing member and an implant component comprises the at least one second securing member.

In the implant in accordance with preferred embodiments of the invention, a separate securing device can be dispensed with because the locking element comprises the at least one first securing member and an implant component comprises the at least one second securing member. Consequently, the locking element can co-operate directly with the implant component in order to become secured. This is effected by means of the securing members in the secured position. In consequence, the locking element exercises a further function over and above that of locking the two implant components relative to each other, namely, the self-securement of an implant component. This simplifies the construction of the implant.

In the implant in accordance with preferred embodiments of the invention, the at least one first securing member and the at least one second securing member are formed such that they are movable relative to each other. After adoption of the locking position by the locking element, they can be transferred from an unsecured position into a secured position. In the secured position, the locking element can be secured against movement in a direction opposed to the locking direction. The at least one first securing member and the at least one second securing member are formed such as to be movable relative to each other for the purposes of transference from the released position into the secured position along a securing direction which is oriented transversely relative to the displacing direction. If a force is acting in the securing direction, this results in the at least one first and the at least one second securing member being transferred relative to each other "automatically" as it were from the released position into the secured position. This simplifies the securement of the locking element in the locking position, and in particular, it does not have to be carried out by an operating surgeon in an additional processing step following the process of locking the implant. A force acting in the securing direction can arise for example in that the spinous processes apply a supporting force, which can be conducted along the spreading direction and is diverted along the securing direction, to the supporting surfaces of the implant in a direction opposed to the spreading force exerted by the implant.

It is expedient if at least one securing member, and preferably all the securing members comprise or form a stop acting in a direction opposed to the locking direction. This enables the implant to be of a simple construction. The respective stops of two securing members, namely, a first securing member on the locking element and a second securing member on the implant component, can co-operate in the secured position of the securing members.

It is of advantage if at least one securing member is in the form of a projection of a carrier incorporating it because this too provides a simple construction of the implant. The carrier for example, is the locking element or the implant component and in particular, it is a fixing element of the implant component which co-operates therewith in the locking position of the locking element for locking the implant. Expediently, the projection comprises at least one stop acting in a direction opposed to the locking direction.

Preferably, at least one securing member is a receptacle formed on a carrier incorporating it because this too enables a simple construction of the implant to be obtained. The carrier likewise is the locking element, the implant component or in particular the fixing element comprised thereby for example. The receptacle expediently comprises at least one stop which acts in a direction opposed to the locking direction.

It is of advantage if the at least one first securing member and the at least one second securing member abut one another in the secured position. This enables effective securement of the locking element in the locking position. In this way for example, a positive fit between the implant component and the locking element in the locking position thereof can be ensured in a direction opposed to the locking direction.

In the unsecured position, the at least one first securing member and the at least one second securing member and/or stops comprised or formed thereby for example can be spaced from each other in order not to co-operate.

It is preferred that the at least one first securing member and the at least one second securing member engage with one another in the secured position because this enables reliable securement of the locking element and, at the same time, a simple construction of the implant. For example, a securing member in the form of a projection engages in a securing member in the form of a receptacle.

In corresponding manner, reliable securement of the locking element with a simple construction of the implant is expediently achieved if the at least one first securing member and the at least one second securing member engage behind one another in the secured position. Expediently hereby, stops comprised or formed by the securing members abut one another.

Preferably, at least one securing member is arranged on the end of the locking element, taken with respect to the extent thereof along the locking direction. It has been shown in practice that this thereby contributes to a simpler construction for the implant. In particular, the locking element can comprise two first securing members which are arranged at the mutually opposite ends thereof.

It is of advantage if at least one securing member and preferably all of the first securing members are formed in one piece manner with the locking element because this enables a simpler construction of the implant to be obtained.

In the implant in accordance with preferred embodiments of the invention, one implant component comprises the at least one second securing member. In a preferred exemplary embodiment of the implant, provision may be made for the second implant component to comprise the at least one second securing member or at least one second securing member.

As an alternative or in addition thereto, provision may be made for the first implant component to comprise at least one second securing member.

It is of advantage if the second implant component has a fixing element which comprises the at least one second securing member and co-operates with the locking element for locking the implant. The fixing element can co-operate with the locking element in the locking position thereof so that the second implant component is locked from a movement to the first implant component that is directed counter to the spreading direction. At the same time, it comprises the at least one second securing member which, in the secured position, co-operates with the at least one first securing member comprised by the locking element for securing the locking element. Consequently, in like manner to the locking element, the fixing element can be effective in two respects, namely, for locking the implant on the one hand and for the securement of the locking element on the other. This permits of a simpler construction for the implant.

It is expedient if the fixing element forms a contact element which abuts the locking element in the locking position thereof. The second implant component can thereby abut against the locking element, which likewise forms a contact element, for locking the implant. This permits the second implant component to lock onto the first implant component in a constructionally simple manner. For this purpose, the contact elements form co-operating stops acting in a direction opposed to the spreading direction.

Preferably, at least one securing member is arranged on the end of the fixing element, taken with respect to the extent thereof along the locking direction. It has been shown in practice that a simpler construction of the implant is thereby possible. In particular, the fixing element can comprise two second securing members which are arranged at the mutually opposite ends thereof.

It is preferred that at least one securing member and in particular, all of the second securing members be formed in one piece manner with the fixing element. This enables the implant to be of simpler construction.

It is expedient if the locking element is plate-like or is substantially plate-like because this also simplifies the construction of the implant. A plate-like or substantially plate-like locking element can effectively form a contact element via which the locking element can abut against the fixing element over an area. This then gives rise to the possibility of providing reliable locking of the implant. It is particularly preferable for example, for the locking element to comprise a plate-like carrier and a projection which protrudes therefrom and forms a securing member.

It is expedient if at least one securing member and preferably all of the securing members and/or the locking element and/or a fixing element of the second implant component which co-operates with the locking element for locking the implant are rigid. Reliable locking of the implant and/or reliable securement of the locking element in the locking position can then be ensured.

Preferably, implant components comprising the locking element and the at least one second securing member each comprise two securing members which co-operate in pairs in the secured position i.e. the locking element comprises two first securing members, and the implant component comprises two second securing members. Reliable securement of the locking element can thereby be ensured.

The locking direction is expediently oriented transversely and in particular perpendicularly to the spreading direction because, in practice, this has proven to be expedient for locking the implant and for the construction thereof.

Likewise, it has proven to be advantageous for the achievement of a simple construction of the implant and reliable locking thereof, if the locking element is formed such that it is displaceable relative to the first implant component and/or relative to the second implant component for the transfer from the release position into the locking position The securing direction is preferably oriented perpendicularly to the locking direction. In consequence, it does not have any components parallel to the locking direction. This then gives rise to the possibility that the at least one securing member and the at least one second securing member only have to implement a maximally short relative movement with respect to one another when transferring from the unsecured position into the secured position so as to enable the locking element to be secured in the locking position. This provides for a simpler construction of the implant on the one hand and reliable securement of the locking element on the other.

Preferably, the at least one first securing member and the at least one second securing member are biased relative to each other along the securing direction in the unsecured position. By virtue of the bias, this gives rise to the possibility for the at least one first securing member and the at least one second securing member to be transferred "automatically" as it were from the released position into the secured position. This then leads to the securement of the locking element in the locking position being effected automatically when the locking element adopts the locking position. This simplifies the handling of the implant considerably. In particular, an operating surgeon is thus saved from having to additionally undertake the securement of the locking element after locking the implant.

For biasing the at least one first securing member and the at least one second securing member relative to each other, provision may be made for e.g. at least one resilient element such as a spring for instance which acts on one securing member. The resilient element can act e.g. with a first end on the locking element and with a second end on a securing member, and/or it can act e.g. with a first end on the implant component and with a second end on a securing member.

Optionally, in the case of an implant in which the securing device comprises at least one first securing member and also at least one second securing member which, after the adoption of the locking position by the locking element, are transferable relative to each other in a securing direction oriented transversely relative to the locking direction from an unsecured position, in which the at least one first securing member and the at least one second securing member do not co-operate, into a secured position, in which the at least one first securing member and the at least one second securing member co-operate for the securement of the locking element, provision may be made for the at least one first securing member and the at least one second securing member to be biased relative to each other along the securing direction in the unsecured position. In this way, the previously described advantage of a sort of automatic securement of the locking element in the locking position can likewise be obtained. This implant differs from the last described advantageous exemplary embodiment of the implant in accordance with preferred embodiments of the invention in that the locking element does not necessarily comprise the at least one first securing member and in that an implant component does not necessarily comprise the at least one second securing member.

It is of advantage if the second implant component is biased relative to the first implant component in a direction opposed to the spreading direction in the locking position of the locking element. There is thus a bias force effective on the implant components which subjects them to a movement relative to each other in a direction opposed to the spreading direction. If, in the locking position, the locking element acts on the first implant component for locking the implant and the second implant component comprises the at least one second securing member, the bias force can be utilised for ensuring a bias between the at least one first securing member and the at least one second securing member. Consequently, the bias of the two implant components relative to each other that is inherent to the implant can be used for the automatic transfer of the securing members from the unsecured position into the secured position. This facilitates the handling of the implant and in addition, it enables simpler construction thereof.

Biasing of the at least one first securing member and the at least one second securing member relative to each other in the unsecured position can also be obtained in that a supporting force exerted by the spinous processes is applied via the supporting surfaces to the two implant components and is conducted along the spreading direction. This supporting force can work in like manner to the previously described bias force so that, when the locking element acts on the first implant component in the locking position and the second implant component comprises the at least one second securing member, biasing of the securing members relative to each other can be obtained in the unsecured position and thus automatic securement of the locking element can also be achieved when it adopts the locking position.

It is preferred that the securing direction have a component parallel to the spreading direction, and expediently that the securing direction be oriented in parallel with the spreading direction. In this way, the previously described bias force or the supporting force along the spreading direction can lead directly i.e. without having to be diverted, to the biasing of the at least one first securing member and the at least one second securing member relative to each other. A device for diverting the bias force or the supporting force can thus be dispensed with. This simplifies the construction of the implant.

It is of advantage if a fixing element of the second implant component which co-operates with the locking element for locking the implant and the locking element each comprise at least one guidance member or form a guidance member which, in the course of transferring the locking element from the release position into the locking position, co-operates with a further guidance member which is formed by the locking element or by the fixing element, or, is comprised by the locking element or by the fixing element. The locking element can thus be transferred in a clearly defined locking direction from the release position into the locking position in a reliable manner.

It is expedient if at least one securing member forms a guidance member because this enables simpler construction of the implant.

It is of advantage if the locking element comprises or forms at least one first application member for subjecting the locking element to a spreading force directed in the spreading direction, and if the locking element comprises or forms at least one second application member for placement on an implant component when transferring the implant from the introduction position into the spread position. This then gives rise to the possibility of using the locking element as a bearing element for the transference of the implant from the introduction position into the spread position. The locking element can be subjected to a spreading force at the at least one first application member, and for its part, it can convey the spreading force by means of the at least one second application member to the implant component. For example, the locking element can convey the spreading force to the previously mentioned fixing element comprised by the second implant component.

Preferably, at least one securing member forms an application member because this makes for a simpler construction of the implant.

The present invention further relates to a surgical system incorporating at least one implant for mutually supporting the spinous processes of adjacent vertebral bodies, comprising a first implant component and a second implant component. The implant is transferable by moving the second implant component relative to the first implant component along a spreading direction from an introduction position, in which the implant is introducible between an upper spinous process of an upper vertebral body and a lower spinous process of a lower vertebral body, into a spread position, in which an upper supporting surface for the upper spinous process that is formed by the implant and a lower supporting surface for the lower spinous process that is formed by the implant have a greater spacing relative to each other than in the introduction position. The implant comprises a locking device incorporating a locking element wherein the locking element is transferable relative to at least one implant component along a locking direction from a release position, in which the second implant component is movable relative to the first implant component in a direction opposed to the spreading direction, into a locking position in which the second implant component is locked to the first implant component against a movement that is directed counter to the spreading direction. The implant also comprises a securing device for securing the locking element against a movement that is directed counter to the locking direction. The securing device comprises at least one first securing member and also at least one second securing member which, following adoption of the locking position by the locking element, are transferable relative to one another in a securing direction that is directed transversely relative to the locking direction from an unsecured position, in which the at least one first securing member and the at least one second securing member do not co-operate, into a secured position in which the at least one first securing member and the at least one second securing member co-operate for securing the locking element. The locking element comprises the at least one first securing member and an implant component comprises the at least one second securing member. The surgical system comprises a handling device for transferring the locking element from the release position into the locking position.

The advantages attainable with the implant can likewise be obtained. These advantages have already been explained in connection with the explanation of the implant in accordance with an aspect of the invention.

Moreover, the surgical system comprises a handling device for transferring the locking element from the release position into the locking position. An operating surgeon can avail himself of this handling device in order to lock the implant. This simplifies the process of locking the implant and, at the same time, increases the user friendliness of the surgical system.

In particular, the surgical system can comprise one of the previously described implants.

It is expedient if the system comprises a coupling device having at least one first coupling member comprised by the locking element and at least one second coupling member comprised by the handling device which co-operate for transferring the locking element from the release position into the locking position. The coupling device makes it possible for the locking element to be transferred from the release position into the locking position by means of the handling device.

It is of advantage if at least one coupling member and preferably all of the coupling members comprise or form a stop which acts in the locking direction because this provides for a simple construction of the coupling device. In particular, the stop is a driving stop which produces the effect that the at least one second coupling member subjects the at least one first coupling member to a force that is in the locking direction in order to transfer the locking element from the release position into the locking position.

Advantageously, at least one coupling member is in the form of a projection of a carrier incorporating it. The carrier may, for example, be the locking element or the handling device. The projection expediently comprises the stop or forms it.

Preferably, at least one coupling member is a receptacle formed on a carrier incorporating it. The carrier is, for example, the locking element or the handling device. The receptacle expediently forms the stop or comprises it.

It is expedient if the at least one first coupling member and the at least one second coupling member abut one another for transferring the locking element from the release position into the locking device. The locking element can thus be transferred into the locking position in a reliable manner. For example, the coupling members abut each other with stops and in particular, driving stops that are formed or comprised thereby.

Provision may be made for the at least one first coupling member and the at least one second coupling member to engage in one another for transferring the locking element from the release position into the locking position. For example, this can be effected in that one coupling member forms a projection and a further coupling member forms a receptacle in which the projection engages.

Likewise, provision may be made for the at least one first coupling member and the at least one second coupling member to engage behind one another for transferring the locking element from the release position into the locking position. Expediently thereby, stops and in particular driving stops formed or comprised by the coupling members abut one another. This provides for reliable transfer of the locking element from the release position into the locking position.

It is of advantage if the at least one first coupling member is arranged on the end of the locking element, taken with respect to the extent thereof along the locking direction. In practice, this has proven to be reliable for producing effective coupling with the handling device.

A simpler construction of the implant is made possible if the at least one first coupling member is formed in one piece manner with the locking element.

It is expedient if, after adoption of the locking position by the locking element, the at least one first coupling member and the at least one second coupling member are transferable relative to each other in an uncoupling direction oriented transversely relative to the locking direction from a coupling position, in which the at least one first coupling member and the at least one second coupling member co-operate for transferring the locking element from the release position into the locking position, into an uncoupling position, in which the at least one first coupling member and the at least one second coupling member do not co-operate. In the coupling position, the at least one first and the at least one second coupling member can co-operate for transferring the locking element into the locking position. Once the locking element adopts the locking position, the coupling members have served their intended purpose. They can decouple from each other, by transferring them relative to each other along an uncoupling direction into an uncoupling position in which they no longer co-operate. This, for example, gives rise to the possibility of extracting or of removing the handling device from the implant after it has been locked because it is no longer needed for the locking of the implant.

In the uncoupling position, the at least one first coupling member and the at least one second coupling member and/or stops comprised or formed thereby may, for example, be spaced from each other in order not to co-operate.

Preferably, the at least one first coupling member and the at least one second coupling member are biased relative to each other along the uncoupling direction in the coupling position. This permits the at least one first coupling member and the at least one second coupling member to decouple from each other "automatically" as it were i.e. to transfer from the coupling position into the uncoupling position. This functions in correspondence with the previously described manner for the case of the at least one first securing member and the at least one second securing member which can be transferred automatically from the unsecured into the secured position as a result of a bias action. In the present case, after adoption of the locking position by the locking element, uncoupling of the at least one first and the at least one second coupling members can be achieved automatically.

For example, biasing of the at least one first coupling member and the at least one second coupling member relative to each other can be based on the biasing of the two implant components relative to each other. In corresponding manner, a supporting force applied by the spinous processes to the implant and acting in a direction opposed to the spreading direction can likewise serve the same purpose. Thereby in particular, this gives rise to the possibility that the bias force or the supporting force can be effective both for automatically transferring the securing members from the unsecured position into the secured position as well as for automatically transferring the coupling members from the coupling position into the uncoupling position.

Preferably, the uncoupling direction has a component parallel to the spreading direction, and expediently, the uncoupling direction is oriented in parallel with the spreading direction. This then gives rise to the possibility that, in the locking position of the locking element, a bias force between the first implant component and the second implant component can act, without having to be deflected, in a direction opposed to the spreading direction for transferring the at least one first coupling member and the at least one second coupling member from the coupling position into the uncoupling position.

In order to enable a bias force or a supporting force to be used for the uncoupling of the coupling members, it may be necessary for the handling device to be coupled to the implant. Expediently, the handling device comprises at least one coupling element for coupling the at least one second coupling member to an implant component in the locking position of the locking element. A bias force or a supporting force acting on the implant component can be conveyed by means of the coupling element to the handling device and in particular, to the at least one second coupling member. At the same time, the bias force or the supporting force can act via the other implant component on the locking element and in particular, on the at least one first coupling member. In this way, the at least one first coupling member and the at least one second coupling member can be biased relative to each other in the coupling position and, after the adoption of the locking position by the locking element, they are automatically transferred into the uncoupling position.

It is expedient if the at least one coupling element couples the at least one second coupling member to a fixing element of the second implant component which co-operates with the locking element for locking the implant. This then gives rise to the possibility of conveying a bias force or a supporting force to the at least one second coupling member via the second implant component and in particular, via its fixing element.

The at least one coupling element is in engagement with the implant component and in particular the fixing element of the second implant component in force-locking and/or positively-locking manner for example. It can, for example, be connected to the at least one second coupling member in one piece manner thereby achieving the coupling effect.

It is of advantage if the handling device comprises a receptacle for the locking element. The receptacle can serve for the protection of and for improved handling of the locking element. The latter can be held in the receptacle for example.

It is preferred that the receptacle comprise an opening through which the locking element is not removable from the receptacle in the coupling position of the at least one first coupling member and the at least one second coupling member and through which the locking element is removable from the receptacle in a direction oriented transversely relative to the uncoupling direction in the uncoupling position of the at least one first coupling member and the at least one second coupling member. In the coupling position, the coupling members co-operate in order to transfer the locking element into the locking position. Meanwhile, the locking element is arranged in the receptacle and cannot be removed therefrom through the opening. After adoption of the locking position by the locking element, the at least one first coupling member and the at least one second coupling member can move along the uncoupling direction into the uncoupling position. The implant is locked by means of the locking element, and the locking element can be removed from the receptacle of the handling device through the opening. This, for example, enables the handling device to be extracted from the implant after it has been locked, for example, along the locking direction oriented transversely relative to the uncoupling direction.

The opening of the receptacle is expediently arranged on the end of the handling device, namely, preferably at the end of the handling device that is located opposite that end of the handling device which is grasped by an operating surgeon for extracting the handling device from the implant.

It is of advantage if the at least one second coupling member at least partly forms an edge of the opening or is arranged thereon because this makes it possible to produce a simpler constructional design for the handling device. The locking element cannot pass through the opening until such time as the coupling members adopt the coupling position, wherein the at least one first coupling member abuts an edge of the opening. Once the coupling members have adopted the uncoupling position, the opening is, as it were, free for the locking element so that it can pass through the opening and be removed from the receptacle.

Preferably, the locking element and a fixing element of the second implant component co-operating with the locking element for locking the implant are arranged in the receptacle so as to be free from play along the uncoupling direction and in particular are arranged therein in positively-locking manner in the coupling position of the at least one first coupling member and the at least one second coupling member, and are arranged in the receptacle with play in the uncoupling position of the at least one first coupling member and the at least one second coupling member. The arrangement of the fixing element in the receptacle in addition to the locking element serves to ensure a reliable relative positioning of the fixing element and the locking element when transferring it from the release position into the locking position. Thereby moreover, the implant is securely retainable on the handling device. In the coupling position of the coupling members, the locking element and the fixing element can adopt a greater spacing relative to each other along the uncoupling direction than in the uncoupling position. In particular hereby, the previously described opening of the receptacle can be dimensioned along the uncoupling position in such a manner that the fixing element and the locking element are removable from the receptacle through the opening in the uncoupling position of the coupling members, whereas they are not removable from the receptacle in the coupling position of the coupling members. When decoupling the coupling members, it can thereby be ensured in a constructionally simple manner that the locking element and the fixing element can be removed from the receptacle through the opening.

It is of advantage if the locking element and/or a fixing element of the second implant component co-operating with the locking element for locking the implant are arranged in the receptacle such as to be free from play along the locking direction and in particular are arranged therein in positively-locking manner when transferring the locking element from the release position into the locking position. This enables more reliable transfer of the locking element from the release position into the locking position. Moreover, a reliable relative positioning of the fixing element and the locking element relative to each other can be ensured. Furthermore thereby, the implant is securely retainable on the handling device.

Preferably, the locking element and/or a fixing element of the second implant component co-operating with the locking element for locking the implant are arranged in the receptacle such as to be free from play in a direction oriented transversely relative to the locking direction and transversely relative to the uncoupling direction and in particular are arranged therein in positively-locking manner when transferring the locking element from the release position into the locking position. This likewise enables more reliable transfer of the locking element from the release position into the locking position. Moreover, reliable relative positioning of the fixing element and the locking element relative to each other can be ensured. Furthermore thereby, the implant is securely retainable on the handling device.

It is of advantage if the receptacle is expandable. This, for example, simplifies the process of attaching the handling device to the implant. If the receptacle is expanded, the locking element and possibly also the fixing element can be inserted more easily into the receptacle.

In particular, provision may be made for the receptacle to be expandable in a direction oriented transversely relative to the locking direction and transversely relative to the uncoupling direction.

It is preferred that the handling device comprise a first arm which engages over the locking element and the fixing element at a first side thereof and also a second arm which engages under the locking element and the fixing element at a second side thereof located opposite the first side, wherein the first arm and the second arm each bound the receptacle to at least a partial extent. The first and the second arm can engage over or under the locking element and the fixing element and define the receptacle therebetween. The locking element and the fixing element are preferably arranged between the first arm and the second arm such as to be free from play and in particular, in positively-locking manner. This then gives rise to the possibility of holding the implant by means of the handling device in order to apply it for instance. Furthermore, the first arm and the second arm can each form a coupling element for coupling the fixing element to at least one second coupling member which can be comprised by the first arm and/or by the second arm. This makes it possible to couple the fixing element to the at least one second coupling member.

It is expedient if the first arm and the second arm engage over or under the locking element and the fixing element at a first end and are connected to one another at a second end remote from the first end. In this case for example, the handling device can have a clip-like shape incorporating the first arm and the second arm which form the receptacle for the locking element and the fixing element therebetween and which are connected, e.g. by means of a web. This then gives rise to the possibility for the first arm to spread relative to the second arm and thereby expand the receptacle. This makes it possible to attach the handling device to the implant in a more simple manner.

Advantageously, the handling device is pre-mounted on the implant because this simplifies the handling thereof.

The handling device can be a component of the implant and be comprised thereby, especially if it is pre-mounted thereon.

It is expedient if the handling device comprises a connecting device for connection to an applicator comprising a gripping element. This makes it possible to connect the applicator to the handling device. The operating surgeon can grasp the applicator by the gripping element in order to actuate the handling device. If, as previously described, the locking element is arranged in the receptacle of the handling device together with the fixing element and in particular, if it is held therein, the operating surgeon can also apply the implant by means of the applicator. In addition, he can grip the applicator in order to transfer the locking element from the release position into the locking position.

In one simple constructional embodiment, the connecting device is in the form of a latching device and particularly, in the form of a releasable latching device.

The handling device is of particularly simple construction when it is formed in one piece manner.

It is of advantage if the handling device comprises or forms at least one third application member for subjecting the locking element to a spreading force oriented in the spreading direction and for placement on at least one first application member comprised or formed by the locking element when transferring the implant from the introduction position into the spread position. The at least one third application member can convey a spreading force to the locking element and in particular to its at least one first application member by subjecting the handling device to a force. This spreading force can be conveyed to the implant component via the at least one second application member of the locking element. The handling device thus forms a bearing element for spreading the implant.

Preferably, the at least one third application member bounds a receptacle for the locking element comprised by the handling device to at least a partial extent because this simplifies the construction of the handling device.

An implant 10 illustrated perspectively in FIGS. 1 to 3 is an inter-vertebral implant for mutually supporting the spinous processes of adjacent vertebral bodies that are not shown in the drawing. It belongs to a class of implants that is described in DE 20 2008 009 344 U1.

The implant comprises a first implant component 12 and also a second implant component 14 which is substantially identical to the first component. The first implant component 12 comprises a first supporting segment 16 which comprises two supporting arms 17 and 18, and also a second supporting segment 19 which comprises a supporting arm 20 that is arranged between the first supporting arm 17 and the second supporting arm 18. The supporting segments 16 and 19 are held together at a first end side 21 of the implant 10 by means of a holding member 22 in the form of a C-shaped clip 23.

In corresponding manner, the second implant component 14 comprises a first supporting segment 24 having two mutually spaced supporting arms 25 and 26 and also a second supporting segment 27 having a supporting arm 28 which is arranged between the supporting arms 25 and 26. The supporting segments 24 and 27 are held together at an end side 29 of the implant 10 located opposite the end side 21 by means of a holding member 30 in the form of a C-shaped clip 31. The holding member 30 is also referred to as a fixing element 32 of the implant component 14.

The implant components 12 and 14 are configured such as to be mirror symmetrical relative to each other with respect to a centre of symmetry that is not illustrated in the drawing. The consequence of this is that the supporting arms 17 and 25, the supporting arms 18 and 26 and also the supporting arms 20 and 28 can abut one another.

Two clamping elements 33 and 34 which are fixed to the clip 23 extend from the end side 21 up to the end side 29 and thereby pass through the implant 10 and in particular the clip 31 at openings which are not illustrated in the drawing. The clamping elements 33 and 34 are connected at the end side 29 by means of a connecting member 35 which, for reasons of clarity, is only illustrated in FIG. 6. The direction in which they extend defines a spreading direction 36 of the implant 10 (FIGS. 4 and 5), and together they form a tie rod 37 of the implant 10.

Commencing from an introduction position that is illustrated in FIG. 1, the implant 10 can be transferred into a spread position that is illustrated in FIGS. 2 and 3 by applying a force to the clip 31 in the spreading direction 36 for example, whereby the second implant component 14 is displaced relative to the first implant component 12 along the tie rod 37. The supporting arms 17 and 25, the supporting arms 18 and 26 and also the supporting arms 20 and 28 thereby slide along one another so that the implant 10 spreads out in a direction oriented perpendicularly to the spreading direction 36. An upper supporting surface 38 formed by the supporting arms 20, 25 and 26 for an upper spinous process and also a lower supporting surface 39 formed by the supporting arms 17, 18 and 28 for a lower spinous process have a greater spacing from each other in this spread position of the implant 10 than in the introduction position. This enables the implant 10 to be inserted between the vertebral bodies through only a small body opening in the introduction position and then to be transferred from the introduction position into the spread position for supporting the spinous processes.

In order to lock the implant 10 in the spread position, the arrangement comprises a locking device 40 having a plate-like locking element 41 which is arranged on the side of the clip 31 facing the end side 29 and defines a plane oriented perpendicularly to the spreading direction 36. The locking element 41 has two through openings 42 and 43. The through openings 42 and 43 each comprise a first section 44 and a second section 45 (FIGS. 1 to 3), wherein the first section 44 is in each case sufficiently large that one of the clamping elements 33 or 34 can pass through it. The second section 45 has a reduced cross section compared with the first section 44.

In this way, when the implant 10 adopts the spread position, this gives rise to the possibility of displacing the locking element 41 relative to the tie rod 37 in a locking direction 46 oriented transversely and in particular perpendicularly to the spreading direction 36 in such a way that the respective second sections 45 of the through openings 43 and 44 can engage in gaps 47 which are formed between locking members 48 arranged on the clamping elements 33 and 34.

The locking members in the form of locking projections 48 form stops for the locking element 41 which can be supported in this way on the first implant component 12 in a direction opposed to the spreading direction 36. The second implant component 14 can thereby be locked to the first implant component 12. This means that, in the locking position of the locking element 41 that is defined in this way, the second implant component 14 is locked to the first implant component 12 against movement in a direction opposed to the spreading direction 36 (FIGS. 3 and 5).

The locking element 41 can be transferred into the locking position from a release position by displacement along the locking direction 46, whereby, in the release position, the implant components 12 and 14 are movable relative to each other along the spreading direction 36 and in the counter direction thereof (FIGS. 1, 2 and 4). Thereby, the clamping elements 33 and 34 engage through the first sections 44 of the through openings 42 and 43.

In order to secure the locking element 41 in the locking position after its adoption thereof against movement in a direction opposed to the locking direction 46 and thus prevent unlocking of the implant 10, the implant 10 comprises a securing device 49.

The securing device 49 comprises a pair of first securing members 50 and 51 which are formed in one piece manner with the locking element 41. They are arranged on opposite ends of the locking element 41, namely, the securing member 50 in the region of the clamping element 33 and the securing member 51 in the region of the clamping element 34. The securing member 50 comprises a stop 52 which acts in a direction transverse to the locking direction 46, and the securing member 51 is in the form of a projection 53 of the locking element 41 having a stop 54 acting transversely relative to the locking direction 46.

In corresponding manner, the implant 10, and in particular the second implant component 14, especially the clip 31, comprises a pair of second securing members 55 and 56. The securing members 55 and 56 are formed in one piece manner with the clip 31. Taken with respect to the locking direction 46, they are arranged at mutually opposite ends of the clip 31, namely, the securing member 55 opposite the securing member 50 in the vicinity of the clamping element 33, and the securing member 56 opposite the securing member 51 in the vicinity of the clamping element 34. The securing member 55 is in the form of a projection 57 which protrudes from the clip 31 in the direction of the locking element 41 and has a stop 58 acting transversely relative to the locking direction 46, and the securing member 56 comprises a stop 59 which acts in a direction transverse to the locking direction 46.

For as long as the locking element 41 adopts the release position and the implant 10 is not locked, the locking element can abut the clip 31 via the securing member 51 and be supported thereon along the spreading direction 36, and the clip 31 can abut the locking element 41 via the securing member 55 and be supported thereon in a direction opposed to the spreading direction 36 (FIG. 4). This can occur automatically for example, if the locking element 41 is subjected to a spreading force acting in the spreading direction 36 for spreading the implant 10. To this end, the locking element 41 forms an extensive application member 60 especially on the side thereof remote from the clip 31. When transferring the implant 10 from the introduction position into the spread position, the securing member 51 and the section 61 of the locking element 41 located opposite the securing member 55 each form a respective second application member 62 or 63. The spreading force acting on the application member 60 can be conveyed to the clip 31 via the application members 62 and 63 and hence spreading of the implant 10, i.e. the transference thereof from the introduction position into the spread position can be effected.

If, in the spread position of the implant 10, the locking element 41 is transferred from the release position into the locking position, the securing members 51 and 55 form respective guidance members 64 and 65 which co-operate with the guidance members 66 and 67 formed by the clip 31 and the locking element 41 (FIG. 4). This ensures reliable transfer of the locking element 41 from the release position into the locking position.

When the locking element 41 adopts the locking position, the securing members 50 and 55 and also 51 and 56 are each movable relative to each other along the spreading direction 36. This is because the locking element 41 can be displaced relative to the clip 31 on the tie rod 37 to just such an extent that the stops 52 and 58 and also the stops 54 and 59 can be arranged along the locking direction 46 exactly adjacent to each other.

For a short length of time, a contact element 68 of the locking element 41 facing the clip 31 and a contact element 69 of the clip 31 facing the locking element 41 adopt a position where the spacing therebetween is defined by the size of the projections 53 and 57 i.e. the securing members 51 and 55.

At the expiry of this short length of time, the securing members 50 and 55 can move relative to each other as can also 51 and 56 move relative to each along the spreading direction 36 which therefore also defines a securing direction so that the stops 52 and 58 and also 54 and 59 come into contact. The securing members 50 and 55 and also 51 and 56 thus co-operate for securing the locking element 41 in the locking position against a movement in a direction opposed to the locking direction 46 (FIG. 5). This defines a secured position of the securing members 50, 51, 55 and 56, and a position of the securing device 49 in which the securing members 50 and 55 and also 51 and 56 do not co-operate defines an unsecured position of the securing members 50, 51, 55 and 56. In the secured position, the locking element 41 and the clip 31 engage behind one another so that the implant 10 is locked and in addition, the locking element 41 is secured in the locking position.

The relative movement of the securing members 50 and 55 and also 51 and 56 to each other can take place automatically with the adoption of the locking position by the locking element 41. This is determined by the fact that the locking element 41 can only adopt the locking position when the implant 10 is in the spread position because the locking projections 48 do not extend over the entire length of the tie rod 37, but are arranged only at a middle region thereof between the end sides 21 and 29. In the spread position, the implant components 12 and 14 are now biased against each other along the spreading direction 36. This is due to the fact that the supporting segments 16, 19, 24 and 27 are formed from a resilient material and are supported on each other. A bias force thereby ensues, this being applied to the first implant component 12, thus to the tie rod 37 and thus to the locking element 41 on the one hand, and to the second implant component 14 and thus to the clip 31 on the other. Immediately after the adoption of the locking position by the locking element 41, the clip 31 and the locking element 41 thus approach one another and hence too the securing members 50 and 55 and also 51 and 56 also approach one another in order to ensure the automatic securement of the locking element 41.

Even in the case of a non-resilient implant, a supporting force applied to the implant components 12 and 14 via the supporting surfaces 38 and 39 could lead to a supporting force which acts along the spreading direction 36 and with the aid of which automatic securement of the locking element 41 in the locking position could be ensured.

A surgical system in accordance with a preferred embodiment of the invention is illustrated perspectively in FIG. 6 and is denoted by the reference symbol 70 therein. The system 70 comprises the previously described implant 10 in accordance with another aspect of the invention and also a handling device 71 with which, inter alia, the locking element 41 is transferable from the release position into the locking position. The handling device 71 is referred to as an adapter 72 in the following.

The adapter 72 comprises a first arm 74 which forms a first holding element 73 for the implant 10 and which can engage over the clip 31 and the locking element 41. The lower surface thereof facing the clip 31 and the locking element 41 is formed in correspondence with the contour of the clip 31 and the contour of the locking element 41 (FIGS. 7 and 9) so that the locking element 41 and the clip 31 can abut the first arm 74 over an area. It protrudes from the implant 10 along the locking direction 46 and is connected at the end thereof remote from the implant 10 by a web-like connecting section 75 to a second arm 77 of the adapter 72 which forms a further holding element 76.

The second arm 77 is mirror-symmetrical relative to the first arm 74 taken with respect to a plane defined by the tie rod 37 so that the second arm 77 can engage under the clip 31 and the locking element 41 and in particular abut them over an area.

In the manner previously described, the adapter 72 forms a sort of clip incorporating the two arms 74 and 77 which define a receptacle 78 for the clip 31 and the locking element 41 therebetween. In the receptacle 78, the clip 31 and the locking element 41 are arranged perpendicular to the spreading direction 36 and perpendicular to the locking direction 46 such as to be free from play and in particular to fit positively therein. This then gives rise to the possibility of holding the implant 10 by means of the adapter 72 so that it can also be introduced into the inter-vertebral space therewith.

The adapter 72 is formed in one piece manner. It can be connected to the implant 10 on delivery, i.e. be pre-mounted thereon. It is also possible for it to be placed on the implant 10 or attached thereto at a later time. To this end, the arms 74 and 77 can be spread apart perpendicularly to the spreading direction 36 and perpendicularly to the locking direction 46 because they are only connected to one another by means of the relatively thin web-like connecting section 75. This then gives rise to the possibility of widening the receptacle 78 in such a way that the adapter 72 can be placed on the implant 10 or attached thereto.

At a point located approximately centrally between the connecting section 75 and the receptacle 78, the adapter 72 comprises a connecting device 79 in the form of a latching device 80. A latching device of an applicator corresponding to the latching device 80 can be latched to the latter device in order to connect the adapter 72 to the applicator. Expediently, an applicator that is to be connected comprises a gripping element in order to make the task of handling the adapter 72 and the implant 10 held thereon simpler for an operating surgeon.

The adapter 72 forms a first bearing element for spreading the implant 10. For this purpose, it comprises two application members 81 and 82 which are formed on the first arm 74 and on the second arm 77. They partly bound the receptacle 78 in the direction of the end side 29 of the implant 10 when the adapter 72 is attached to the implant 10. The application members 81 and 82 can subject the application member 60 formed by the locking element 41 to a spreading force acting in the spreading direction 36. When the locking element 41 adopts the release position, this spreading force can be conveyed via the application members 62 and 63 to the clip 31 and thus to the second implant component 14. The adapter 72 can thus be used as a bearing element for transferring the implant 10 from the introduction position into the spread position by moving it along the spreading direction 36.

The receptacle 78 of the adapter 72 is dimensioned along the spreading direction 36 such that the locking element 41 and the clip 31 are arranged in the receptacle 78 so as to be free from play along the spreading direction 36 and in particular so that they fit positively in the receptacle 78 at least when the locking element 41 adopts the release position (FIGS. 7 and 8). This provides for reliable holding of the implant 10 on the applicator 72 and reliable transference of the implant 10 from the introduction position into the spread position.

In the release position, the locking element 41 is free from play along the locking direction 46 and in particular, it is held in a positively-locking manner in the receptacle 78. For this purpose, the adapter 72 comprises a first stop element 83 on the first arm 74 and also a second stop element 84 on the second arm 77. The stop elements 83 and 84 are each arranged at an edge 85 of an opening 86 in the receptacle 78. The opening 86 is formed at the end of the adapter 72 opposite the connecting section 75. The stop elements 83 and 84 thus partially bound sections of the opening 86.

The opening 86 is dimensioned along the spreading direction 36 such that, when the locking element 41 is in the release position wherein the contact elements 68 and 69 are spaced from one another, the clip 31 and the locking element 41 cannot be removed from the receptacle 78. By contrast, the opening 86 is just large enough that, when the contact elements 68 and 69 abut each other, the clip 31 and the locking element 41 can be removed from the receptacle 78 through the opening 86. This means that removal of the clip 31 and the locking element 41 from the receptacle 78 is possible when the securing members 50, 51, 55 and 56 adopt the secured position and the locking element 41 is secured against movement in a direction opposed to the locking direction 46, but not beforehand. Consequently the clip 31 and the locking element 41 cannot be removed from the receptacle 78 even when the locking element 41 has adopted the locking position but the securing members 50, 51, 55 and 56 are still in the unsecured position because in this case too, the contact elements 68 and 69 are still spaced from each other. In the latter case, the locking element 41 even in the locking position and the clip 31 are still arranged in the receptacle 78 such as to be free from play along the spreading direction 36 and in particular so as to fit positively therein.

Over and above the functions that have already been described, the adapter 72 serves for transferring the locking element 41 from the release position into the locking position. For this purpose, the surgical system 70 comprises a coupling device 87. The coupling device 87 comprises two first coupling members 88 and 89 which are each comprised by the locking element 41 and are connected thereto in one piece manner. They are arranged at the end of the locking element 41 incorporating the securing member 50 and comprise respective stops 90 and 91 which act transversely relative to the locking direction 46 (FIG. 9).

Furthermore, the coupling device 87 comprises two second coupling members 92 and 93 which are formed by the stop elements 83 and 84. The coupling members 92 and 93 comprise stops 94 and 95 acting transversely relative to the locking direction 46, and they form drivers 96 and 97 for the locking element 41 (FIGS. 7 and 8).

In the release position of the locking element 41 and in the locking position thereof but only for so long as the securing members 50, 51, 55 and 56 are still in the unsecured position, the coupling members 88 and 92 and also 89 and 93 can abut each other, whereby the stops 90 and 94 and the stops 91 and 95 co-operate. This defines a coupling position of the coupling members 88, 89, 92 and 93. If the adapter 72 is subjected to a force acting in the locking direction 46, the locking element 41 is likewise moved in the locking direction 46 by the effect of the coupling device 87. This continues until such time as the locking element 41 adopts the locking position. Immediately afterwards, as previously explained, the securing members 50, 51, 55 and 56 are transferred from the unsecured position into the secured position wherein the clip 31 and the locking element 41 come into contact by means of the respective contact elements 69 and 68 due to the effect of the bias of the implant components 12 and 14 relative to each other (FIG. 10).

When the locking element 41 adopts the locking position, the coupling members 88 and 92 and also 89 and 93 are movable relative to each other in an uncoupling direction 98 oriented parallel to the spreading direction 36. This follows on the one hand from the fact that the coupling members 88 and 89 are comprised by the locking element 41 which acts on the first implant component 12 held in the locking position. On the other hand, this follows from the fact that the arms 74 and 77 overlap or extend under the clip 31 in positively-locking manner whilst, at the same time, they comprise the coupling member 92 and the coupling member 93. The section 99 of the arm 74 bounding the receptacle 78 on the upper side thus forms a coupling element 100, and the section 101 of the arm 77 bounding the receptacle 78 on the lower side forms a coupling element 102 in corresponding manner. The coupling members 92 and 93 are thus coupled to the clip 31 and hence to the second implant component 14 via the coupling elements 100 and 102.

A movement of the clip 31 and the locking element 41 towards one another due to the bias of the implant components 12 and 14 relative to each other then leads automatically to a relative movement of the coupling members 88 and 92 and also 89 and 93 relative to each other. This occurs precisely when the securing members 50, 51, 55 and 56 are transferred from the unsecured position into the secured position. At this moment, the coupling members 88 and 92 and also 89 and 93 are automatically transferred relative to each other from the coupling position into an uncoupling position in which the stops 90 and 94 or 91 and 95 are spaced relative to each other and consequently no longer co-operate.

As in the case of the securing members 50, 51, 55 and 56, this automatic uncoupling of the coupling members 88, 89, 92 and 93 from each other is based on their bias relative to each other when the locking element 41 adopts the locking position. This bias is to be attributed to the bias of the implant components 12 and 14 relative to each other in the spread position of the implant 10.

If the implant components 12 and 14 are not biased relative to each other in the spread position of the implant 10, then nevertheless a supporting force of the spinous processes that is effective on the supporting surfaces 38 and 39 can be applied along the spreading direction 36. Apart from the previously addressed process for the automatic securement of the locking element 41, this likewise leads to the automatic uncoupling of the adapter 72 from the locking element 41.

When the locking element 41 adopts the locking position, the securing members 50, 51, 55 and 56 the secured position and the coupling members 88, 89, 92 and 93 the uncoupling position, then the contact elements 68 and 69 abut one another. The clip 31 and the locking element 41 can therefore be removed from the receptacle 78 through the opening 86. This is effected by further application of force to the adapter 72 in the locking direction 46. The adapter 72 can then be extracted from the implant 10 following the automatic locking of the implant 10 and the automatic uncoupling of the locking element 41 (FIG. 9).

The invention claimed is:

1. An implant for mutually supporting the spinous processes of adjacent vertebral bodies comprising:
   a first implant component and a second implant component,
   wherein the implant is transferable by moving the second implant component relative to the first implant component along a spreading direction from an introduction position, in which the implant is introducible between an upper spinous process of an upper vertebral body and a lower spinous process of a lower vertebral body, into a spread position, in which an upper supporting surface for the upper spinous process that is formed by the implant and a lower supporting surface for the lower spinous process that is formed by the implant have a greater spacing relative to each other than in the introduction position,
   and comprising a locking device incorporating a locking element wherein the locking element is transferable relative to at least one implant component along a locking direction from a release position, in which the second implant component is movable relative to the first implant component in a direction opposed to the spreading direction, into a locking position in which the second implant component is locked to the first implant component against a movement that is directed counter to the spreading direction,
   and also comprising a securing device for securing the locking element against a movement that is directed counter to the locking direction, wherein the securing device comprises at least one first securing member and also at least one second securing member which, following adoption of the locking position by the locking element, are transferable relative to one another in a securing direction that is directed transversely relative to the locking direction from an unsecured position, in which the at least one first securing member and the at least one second securing member do not co-operate, into a secured position in which the at least one first securing member and the at least one second securing member co-operate for securing the locking element, and wherein the locking element comprises the at least one first securing member and one of the first implant component and the second implant component comprises the at least one second securing member.

2. An implant in accordance with claim 1, wherein at least one of the at least one first securing member and the at least one second securing member comprises or forms a stop which acts in a direction opposed to the locking direction.

3. An implant in accordance with claim 1, wherein at least one of the at least one first securing member and the at least one second securing member is in the form of a projection of a carrier incorporating it.

4. An implant in accordance with claim 1, wherein the at least one first securing member and the at least one second securing member abut one another in the secured position.

5. An implant in accordance with claim 1, wherein at least one of the at least one first securing member and the at least one second securing member is arranged on the end of the locking element taken with respect to the extent thereof along the locking direction.

6. An implant in accordance with claim 1, wherein at least one of the at least one first securing member and the at least one second securing member is formed in one piece manner with the locking element.

7. An implant in accordance with claim 1, wherein the second implant component comprises the at least one second securing member.

8. An implant in accordance with claim 7, wherein the second implant component has a fixing element which co-operates with the locking element for locking the implant and which comprises at least one second securing member.

9. An implant in accordance with claim 8, wherein the fixing element forms a contact element abutting the locking element in the locking position thereof.

10. An implant in accordance with claim 8, wherein at least one of the at least one first securing member and the at least one second securing member is arranged on the end of the fixing element, taken with respect to the extent thereof along the locking direction.

11. An implant in accordance with claims 8, wherein at least one of the at least one first securing member and the at least one second securing member is formed in one piece manner with the fixing element.

12. An implant in accordance with claim 1, wherein the locking element is plate-like or substantially plate-like.

13. An implant in accordance with claim 1, wherein at least one of the at least one first securing member and the at least one second securing member and the locking element and a fixing element of the second implant component co-operating with the locking element for locking the implant are rigid.

14. An implant in accordance with claim 1, wherein the locking element and the implant component comprising the at least one second securing member each comprise two securing members which co-operate in pairs in the secured position.

15. An implant in accordance with claim 1, wherein the locking element and the implant component comprising the at least one second securing member engage behind one another in the secured position.

16. An implant in accordance with claim 1, wherein the locking direction is oriented transversely relative to the spreading direction.

17. An implant in accordance with claim 1, wherein the locking element is formed such as to be displaceable relative at least one of the first implant component and the second implant component for transferring from the release position into the locking position.

18. An implant in accordance with claim 1, wherein the securing direction is oriented perpendicularly to the locking direction.

19. An implant in accordance with claim 1, wherein the at least one first securing member and the at least one second securing member are biased relative to each other along the securing direction in the unsecured position.

20. An implant in accordance with claim 1, wherein the second implant component is biased relative to the first implant component in a direction opposed to the spreading direction in the locking position of the locking element.

21. An implant in accordance with claim 1, wherein the securing direction has a component parallel to the spreading direction.

22. An implant in accordance with claim 1, wherein a fixing element of the second implant component which co-operates with the locking element for locking the implant and the locking element each form at least one guidance member or comprise a guidance member which, when transferring the locking element from the release position into the locking position, co-operates with a further guidance member which is formed by the locking element or by the fixing element or is comprised by the locking element or the fixing element.

23. An implant in accordance with claim 22, wherein at least one of the at least one first securing member and the at least one second securing member forms a guidance member.

24. A surgical system comprising:
at least one implant for mutually supporting the spinous processes of adjacent vertebral bodies comprising a first implant component and a second implant component,
wherein the implant is transferable by moving the second implant component relative to the first implant component along a spreading direction from an introduction position, in which the implant is introducible between an upper spinous process of an upper vertebral body and a lower spinous process of a lower vertebral body, into a spread position, in which an upper supporting surface for the upper spinous process that is formed by the implant and a lower supporting surface for the lower spinous process that is formed by the implant have a greater spacing relative to each other than in the introduction position,
and the implant comprising a locking device incorporating a locking element wherein the locking element is transferable relative to at least one implant component along a locking direction from a release position, in which the second implant component is movable relative to the first implant component in a direction opposed to the spreading direction, into a locking position in which the second implant component is locked to the first implant component against a movement that is directed counter to the spreading direction,
and the implant also comprising a securing device for securing the locking element against a movement that is directed counter to the locking direction, wherein the securing device comprises at least one first securing member and also at least one second securing member which, following adoption of the locking position by the locking element, are transferable relative to one another in a securing direction that is directed transversely relative to the locking direction from an unsecured position, in which the at least one first securing member and the at least one second securing member do not co-operate, into a secured position in which the at least one first securing member and the at least one second securing member co-operate for securing the locking element, and wherein the locking element comprises the at least one first securing member and one of the first implant component and the second implant component comprises the at least one second securing member, wherein the surgical system also comprises a handling device for transferring the locking element from the release position into the locking position.

25. A surgical system in accordance claim 24, wherein the handling device is pre-mounted on the implant.

* * * * *